US00PP14398P29

(12) United States Plant Patent
Carruth

(10) Patent No.: US PP14,398 P2
(45) Date of Patent: Dec. 23, 2003

(54) HYBRID TEA ROSE PLANT NAMED 'WEKSUNSPAT'

(50) Latin Name: *Rosa hybrida*
Varietal Denomination: WEKsunspat

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 10/243,203

(22) Filed: Sep. 13, 2002

(51) Int. Cl.[7] ..... A01H 5/00
(52) U.S. Cl. ..... Plt./134
(58) Field of Search ..... Plt./134

(56) References Cited

U.S. PATENT DOCUMENTS

PP9,591 P * 6/1996 Strickland ..... Plt./134
PP9,718 P * 12/1996 Fryar ..... Plt./130

OTHER PUBLICATIONS http://www.helpmefind.com/rose/pl.php?n=39717.*
http://www.dirtgardner.com/Roses–NewIntroductions/Rose2003/MarilynMonroe.html.*

* cited by examiner

*Primary Examiner*—Bruce R. Campell
*Assistant Examiner*—W C Haas
(74) *Attorney, Agent, or Firm*—Christie, Parker & Hale, LLP

(57) ABSTRACT

A new variety of Hybrid Tea rose plant suitable for garden decoration, having flowers of soft apricot washed with green coloration.

1 Drawing Sheet

Botanical designation: Rosa hybrida.

BACKGROUND OF THE INVENTION

This invention relates to a new and distinct variety of Hybrid Tea Rose. The varietal denomination of the new variety is 'WEKsunspat'. It has as its seed parent the variety known as 'FRYxotic' (U.S. Plant Pat. No. 9,718) and as its pollen parent the variety known as 'WEKamanda' (U.S. Plant Pat. No. 9,591).

SUMMARY OF THE INVENTION

Among the features which distinguish the new variety from other presently available commercial rose cultivars known to the inventor are the following combination of characteristics: its many stipitate glands at the base of the foliole on the petiolule, its green tones on the outermost petals, its broad variation in stem length and leaf size, its small and large prickles on the peduncle and its long vase life. The plant has a somewhat upright to moderately spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKsunspat' may be asexually propagated by cuttings, budding and grafting.

COMPARISON WITH PARENTS

The new rose may be distinguished from its seed parent, 'FRYxotic' by the following combination of characteristics: whereas 'WEKsunspat' produces double flowers (about 23 to about 30 petals) of soft apricot washed with green, 'FRYxotic' bears apricot pink flowers with significantly higher petalage (about 36 to about 40). The new variety has a moderately rough peduncle, with some stipitate glands, a few small prickles and often one to two large prickles, and bear several large prickles on the major stems, whereas the seed parent has an almost entirely smooth peduncle, with very few stipitate glands, and bears significantly less large prickles on the major stems.

The new variety may be distinguished from its pollen parent, 'WEKamanda' by the following combination of characteristics: whereas 'WEKsunspat' produces double flowers (about 23 to about 30 petals) of soft apricot washed with green, 'WEKamanda' bears yellow gold flowers shaded with green of significantly higher petalage (about 43 to about 49 petals). The new variety has a somewhat upright to moderately spreading medium to tall mature growth habit (about 160 to about 200 cm. in height), whereas the pollen parent has a bushy more upright significantly shorter mature growth habit (about 95 to about 130 cm in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of August. Phenotypic expression may vary with environmental, cultural and climatic conditions, as well as differences in conditions of light and soil.

FLOWER

The new variety usually bears its flowers singly, sometimes in clusters of two per stem. Flowers may be borne in irregular clusters on strong somewhat short to medium length stems (about 36 to about 76 cm.). Outdoors, the plant blooms abundantly and nearly continuously during the growing season. The flowers have a slight tea fragrance.

BUD

The peduncle is about 3.0 to about 4.7 cm. in length, of average caliper (about 0.3 to about 0.4 cm. in diameter), usually erect and stiff. It is moderately rough, with some stipitate glands, a few small prickles and often one to two large prickles. Prickle shape and coloration is similar to that of the prickle shape and coloration on the branches. Peduncle color is between 144A and 146B sometimes very lightly suffused, especially on the side exposed to the sun, with between 187C and 183C.

Before the calyx breaks, the bud is about 2.1 to about 2.5 cm. in diameter at the widest point, about 2.7 to about 3.3 cm. in length, and pointed to somewhat ovoid in shape. The surface of the bud bears few foliaceous appendages and few stipitate glands, usually with slender entire foliaceous parts extending beyond the tip of the bud about ¼ or more of its length. Bud color is between 144A and 143A sometimes very lightly suffused, especially on the side exposed to the sun, with between 187C and 183C.

The sepals are about 2.3 to about 3.0 cm. in length and about 0.7 to about 1.1 cm. in width at the widest point. The outer surface of the sepal is between 144A and 143A sometimes very lightly suffused, especially on the side exposed to the sun, with between 187C and 183C. The inner surface of the sepal is between 147C and 138B and covered with fine wooly tomentum; sepal margins are lined with numerous hairs.

As the petals open (after the calyx breaks), the bud is about 2.7 to about 3.2 cm. in diameter at the widest point, about 3.7 to about 4.1 cm. in length, and very pointed to somewhat ovoid in form. The color of the under surfaces of the newly opened petals is between 24C and 23D, often washed with between 145B and 145C. At the point where the petal attaches on the under surfaces of the newly opened petal, there is a very large zone of between 13B and 13C. At the point where the petal attaches, on the upper surface of the newly opened petals, there is a large zone of between 14B and 12A that gradually suffuses to between 23C and 24C usually lightly overwashed at the very center of the petals with near 29C.

BLOOM

When fully open, the bloom ranges from about 9.6 to about 12.5 cm. in diameter. Petalage is double with about 23 to 30 petals and about 2 to 6 petaloids irregularly arranged. When partially open, the bloom form is high centered to somewhat globular, and the petals spiraled to somewhat cupped with petal edges moderatly reflexed outward. When fully open, the bloom form is more cupped, and the petals are more loosely cupped with petal edges more reflexed outward especially on the outermost petals.

PETALS

The substance of the petals is moderately heavy to somewhat leathery and of medium thickness, with upper surfaces slightly shiny and under surfaces very slightly shiny to more matte. The outer petals are nearly round to somewhat ovate in shape with rounded apices. The inner petals are moderately obovate to somewhat ovate in shape with rounded apices. The petals are about 4.0 to about 5.7 cm. in length and about 3.3 to about 5.9 cm. in width at the widest point. Petal margins are entire.

NEWLY OPENED FLOWER

The under and upper surface of the outer petals is between 19D and 18D, sometimes washed with between 145B and 145C.

The under and upper surface of the intermediate and inner petals is between 24D and 23D. Sometimes the upper surface is lightly overwashed at the very center of the petals with near 29C.

At the point where the petal attaches, there is a moderately large zone of between 9B and 7C.

The general tonality of the newly opened flower is between 24D and 23D.

THREE-DAY-OLD FLOWER

The under and upper surface of the outer petals is between 19D and 27D, sometimes washed with between 145B and 145C.

The under and upper surface of the inner petals is between 27C and 27D.

At the point where the petal attaches, there is a moderately large zone of between 6D and 4C.

The general tonality of the three-day-old flower is between 27C and 27D.

On the spent bloom, the petals usually drop off cleanly.

In August in Upland, Calif., blooms on the bush growing outdoors generally last about five or more days. Cut roses from plants grown outdoors and kept at normal indoor living temperatures generally last about five or more days.

MALE REPRODUCTIVE ORGANS

Stamens are many in number (average about 179) and are arranged regularly about the pistils; a few are mixed with petaloids. The filaments are of various length (about 0.4 to about 0.9 cm.), most with anthers. Filaments are near 9A at the base suffusing to between 25B and 24B. The anthers are moderately small for the class and all open approximately at the same time. Anther color is near 16B when immature and between 200C and 167B at maturity. Pollen is abundant.

FEMALE REPRODUCTIVE ORGANS

Pistils vary in number (average about 146). The styles are moderately even, somewhat short in length (about 0.3 to about 0.5 cm.), somewhat thin in caliper, and moderately bunched. Stigma color is near 11B. Style color is near 1D sometimes suffused near the top with between 53B and 53D. Ovaries are usually all enclosed in the calyx.

Hips are of average length (about 2.2 to about 3.2 cm.), somewhat flat at the top and moderately globular in form, and between 25A and 28B in color when ripe. The hip surface is very smooth with few hairs and few stipitate glands and with thick fleshy walls. The sepals are moderately permanent. The seeds are irregularly rounded, smooth in texture, approximately 20 to about 25 per hip, about 0.3 to about 0.5 cm. in diameter at the widest point and between 160C and 162C in color when mature.

FOLIAGE

The compound leaves are usually comprised of three to five and sometimes seven leaflets and are borne abundantly. The five-leaflet leaves are about 7.2 to about 14.0 cm. in length and about 4.5 to about 12.1 cm. in width at the widest point, moderately leathery to crisp in texture, and somewhat semi-glossy in finish. The terminal leaflets are about 4.3 to about 7.5 cm. in length and about 2.8 to about 5.2 cm. in width at the widest point, shaped very ovate to somewhat oval with moderately acute to somewhat acuminate apices and mostly round to slightly acute bases. The margins are usually simply serrate.

The upper surface of the mature leaf is between 147A and 137B. The under surface of the mature leaf is between 138B and 147C. The upper and under surface of the young leaf is between 144A and 144B, usually heavily suffused with between 187B and 183B on the upper surface and between 183D and 183C on the under surface.

The rachis is of average caliper and moderately rough. The upper side is shallowly grooved with some stipitate glands on the edges of the grooves. The under side of the rachis is moderately rough with many stipitate glands and some small to medium sized prickles. The rachis color is between 145A and 144B.

The stipules are about 1.2 to about 2.0 cm. in length and of somewhat narrow width (about 0.5 to about 0.7 cm.) with medium straight points that usually turn out at an angle of more than 45 degrees often moderately recurved toward the stem. The stipule color is between 145B and 144B.

The petiole is about 0.5 to about 1.5 cm. in length and about 0.1 to about 0.3 cm in diameter at the widest point. The petiole color is between 145B and 144B. At the base of the foliole, on the petiolule, there are many stipitate glands.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a somewhat upright to moderately spreading medium tall growing habit (about 160 to about 200 cm. in height and about 88 to about 110 cm. spread at the widest point), with full branching. It displays moderately vigorous growth and the canes are of somewhat medium caliper for the class.

The color of the major stems is between 146B and 148A. They bear several large prickles that are about 0.9 to about 1.4 cm. in length. The large prickles are angled slightly downward with a moderately long broad oval base; prickle color is between 164A and 165B. The major stems bear some small prickles of similar shape and coloration.

The color of the branches is between 144B and 144A. They bear many large prickles that are about 0.7 to about 1.2 cm. in length. The large prickles are angled slightly downward with a moderately long broad oval base; prickle color is between 145B and 160A. The branches bear some small prickles of similar shape and coloration.

The color of the new shoots is between 144B and 143C sometimes lightly suffused with between 187C and 183D. They bear many large prickles which are of similar size and shape to the large prickles on the branches; prickle color is between 145B and 144A sometimes suffused with between 187C and 183D. The shoots bear many small prickles of similar shape and coloration.

I claim:

1. A new and distinct Hybrid Tea rose plant of the variety substantially as described and illustrated herein.

* * * * *

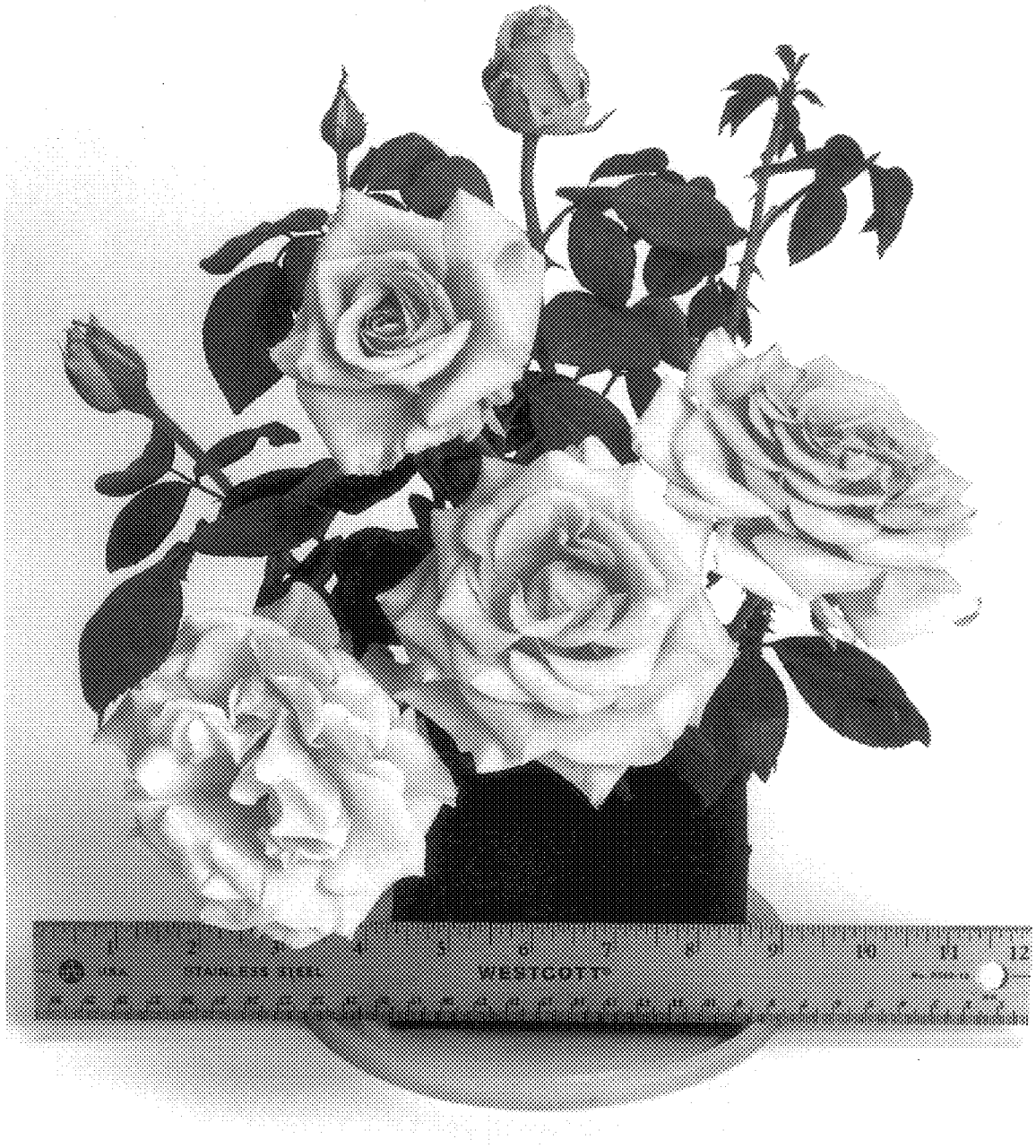
WESTCOTT